United States Patent [19]

Yamada et al.

[11] 4,371,621
[45] Feb. 1, 1983

[54] MICROBIAL POLYAMINE OXIDASE AT-1

[75] Inventors: Hideaki Yamada; Yoshiki Tani; Kimiyasu Isobe, all of Kyoto, Japan

[73] Assignee: Amano Pharmaceutical Co., Ltd., Nagoya, Japan

[21] Appl. No.: 216,301

[22] Filed: Dec. 12, 1980

[30] Foreign Application Priority Data

Dec. 24, 1979 [JP] Japan .................. 54-166952

[51] Int. Cl.³ .................. C12R 1/82; C12R 1/66; C12R 21/00
[52] U.S. Cl. .................. 435/191; 435/913; 435/68
[58] Field of Search .................. 435/68, 189, 199, 913, 435/935; 424/90

[56] References Cited

FOREIGN PATENT DOCUMENTS 55-5096093  7/1980  Japan .................. 435/191

OTHER PUBLICATIONS

Hölta, E. Oxidation of Spermidine and Spermine in Rat Liver: Purification and Properties of Polyamine Oxidase Biochemistry, vol. 16, 1977, pp. 91–100.
Yamaguchi, et al., Isolation and Purification of Blasticdin S. Deaminase from Aspergillus Terrus J. of Antibiotics, vol. 28, 1975, pp. 7–14.
Yamada, et al., Oxidation of Polyamines by Fungal Enzymes, Agric. Biol. Chem., vol. 44, 1980, pp. 2469–2476.
Hill, J. M., Diamine Oxidase (Pea Seedling) *Methods in Enzymology* 17B, 1971 Academic Press, Inc. New York, pp. 730–735.
Yamada, et al., Monoamine Oxidase, *The Journal of Biological Chemistry*, vol. 237, 1962, pp. 1511–1516.
Tabor et al., Identification of Flavin Adenine Dinucleotide and Heme in a Homogeneous Spermidine Dehydrogenase from Serratia Marcescens *The Journal of Biological Chemistry*, vol. 245, 1970, pp. 5424–5433.
Smith, T. A., Purification and Properties of the Polyamine Oxadase of Barly Plants, *Phytochemistry*, 1972, vol. 11, pp. 899–910.
Mann, P. J., Further Purification and Properties of the Amine Oxidase of Pea Seedlings, *Biochem. J. (1961) vol. 79, pp. 623–631.*
Razin et al., The Degradation of Natural Polyamines and Diamines by Bacteria, *Biochemical Journal,* vol. 71, (1959) 551–558.
Smith et al., Further Properties of the Polyamine Oxidase of Barley Leaves, *Phytochemistry,* vol. 13. 1974, pp. 2437–2443.

*Primary Examiner*—Thomas G. Wiseman
*Assistant Examiner*—Kathleen S. McCowin
*Attorney, Agent, or Firm*—Browdy & Neimark

[57] ABSTRACT

A novel polyamine oxidase, polyamine oxidase AT-1, takes an important role participating in decomposition and metabolism of polyamines such as spermidine and spermine.

1 Claim, 5 Drawing Figures

MICROBIAL POLYAMINE OXIDASE AT-1

DETAILED DESCRIPTION OF THE INVENTION

The present invention relates to novel polyamine oxidase AT-1 derived from a microorganism. Polyamine oxidases are ordinarily enzymes having a catalytic activity for oxidative deamination of polyamines, and in the living body they take an important role participating in decomposition and metabolism of polyamines such as spermidine and spermine.

BACKGROUND OF THE INVENTION

Recently, the interrelation between cancer and an increase of amounts of polyamines in body fluids such as blood, urine and lymph has attracted attention, and the use of a polyamine oxidase as an enzyme for diagnosis of cancers has been developed (see Japanese Patent Application Laid-Open Specification No. 9492/75).

Polyamine oxidases derived from animal and plant tissues as supply sources have heretofore been used. However, each polyamine oxidase derived from animal and plant tissues is poor in activity, and they are difficult to obtain in large quantities. Furthermore, it is very difficult to produce these polyamine oxidases at low costs on an industrial scale.

SUMMARY OF THE INVENTION

As the result of research made with a view to developing a process capable of producing a polyamine oxidase at a low cost on an industrial scale, it has now been found that when *Aspergillus terreus* IFO 6346, which is capable of growing with spermidine or spermine as a single carbon-nitrogen source, or a single carbon or single nitrogen source is cultured in a culture medium containing spermidine or spermine, a novel polyamine oxidase AT-1 is produced and accumulated in a large quantity in the culture product; and the present invention is based on this finding.

DETAILED DESCRIPTION OF EMBODIMENTS

Microbial polyamine oxidase AT-1 according to the present invention has the following physicochemical properties.

(1) Reactivity:

As shown by the following reaction formula, the oxidase effects reaction of $CO_2$ and $H_2O$ with spermidine to form 1 mol of putrescine, 1 mol of 3-aminopropionaldehyde and 1 mol of hydrogen peroxide from 1 mol of spermidine, and the oxidase effects reaction of $CO_2$ and $H_2O$ with spermine to form 1 mol of putrescine, 2 mols of 3-aminopropionaldehyde and 2 mols of hydrogen peroxide.

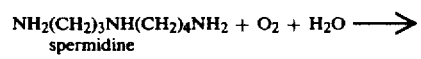
spermidine

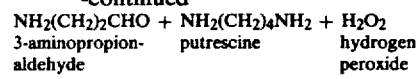
3-aminopropion-   putrescine   hydrogen
aldehyde                       peroxide

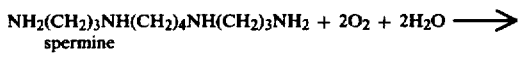
spermine

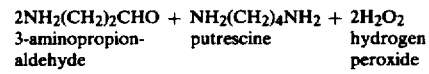
3-aminopropion-   putrescine   hydrogen
aldehyde                       peroxide (2) Substrate Specificity:

As shown in Table 1, the oxidase reacts specifically with spermidine and spermine.

TABLE 1

| Substrate (2 mM) | Relative Activity (%) |
|---|---|
| Methylamine | 0.0 |
| Ethylamine | 0.0 |
| Propylamine | 0.0 |
| Butylamine | 0.0 |
| Phenethylamine | 0.0 |
| Tyramine | 0.0 |
| Dopamine | 0.0 |
| Tryptamine | 0.0 |
| Serotonin | 0.0 |
| Benzylamine | 0.0 |
| Histamine | 0.0 |
| Agmatine | 0.0 |
| Cadaverine | 0.0 |
| Putrescine | 0.0 |
| Spermidine | 100 |
| Spermine | 50.0 |

Figure 1:
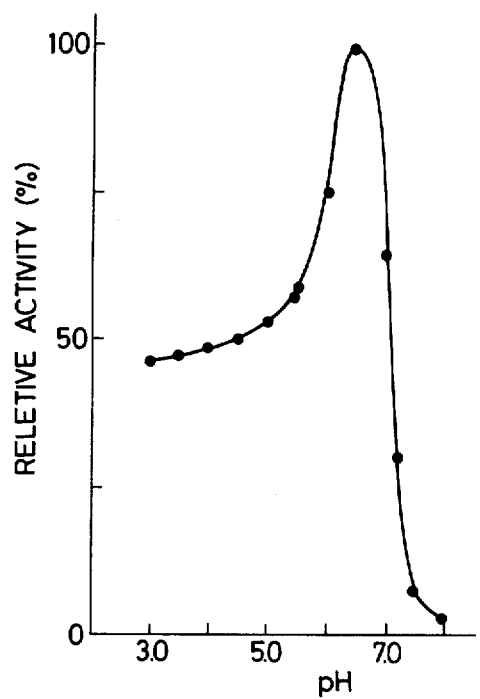
FIG. 1 is a pH activity curve of polyamine oxidase AT-1 of the present invention.

(3) Optimum pH Value:

The optimum pH value is about 6.5 (see FIG. 1).

Figure 2:
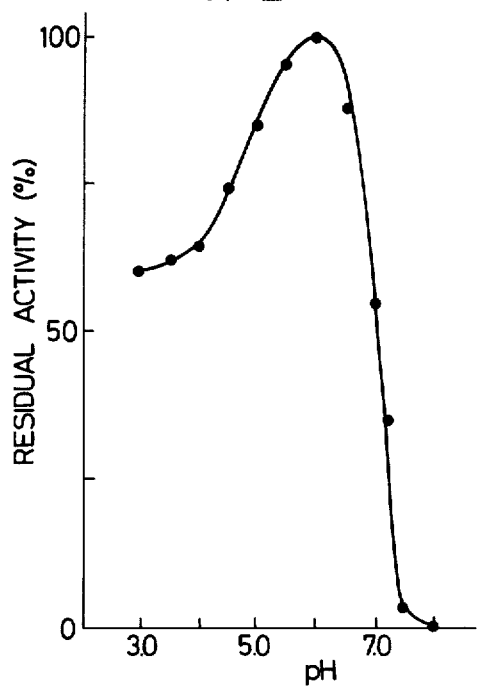
FIGS. 2, 3 and 4 show the pH stability, optimum temperature and temperature stability, respectively.

(4) pH Stability:

When the oxidase is treated at 30° C. for 30 minutes at a pH value of 5.2 to 6.5, the residual ratio of the activity is higher than 90% (see FIG. 2).

Figure 3:
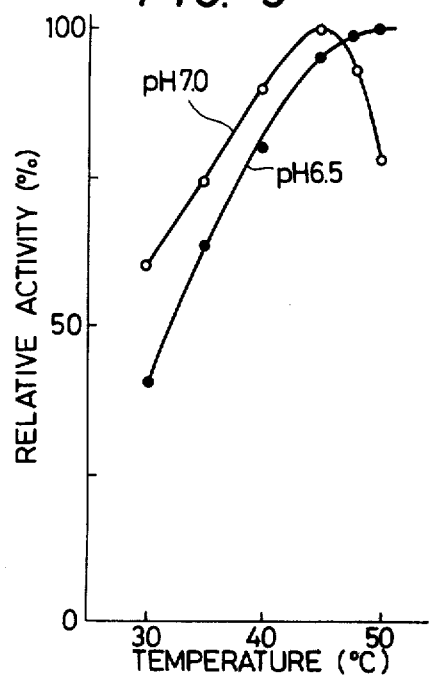

(5) Optimum Temperature:

The optimum temperature is about 50° C. at a pH value of 6.5, and the optimum temperature is about 45° C. at a pH value of 7.0 (see FIG. 3).

Figure 4:
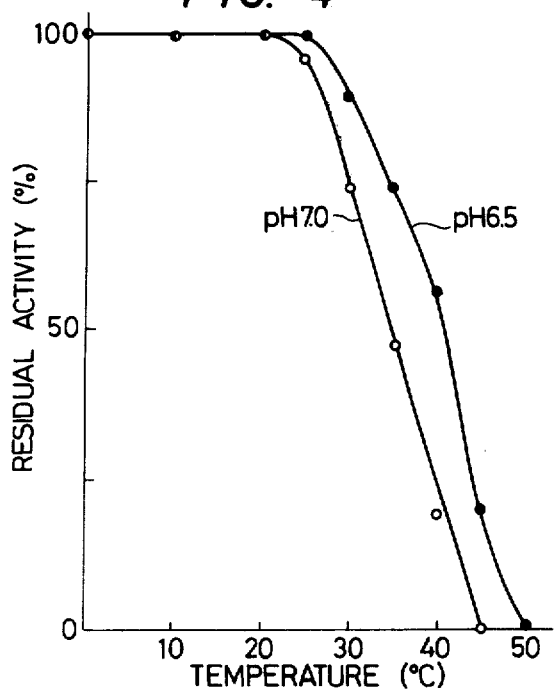

(6) Temperature Stability:

When the oxidase is treated at 30° C. for 10 minutes at a pH value of 6.5, the residual ratio of the activity is higher than 90% (see FIG. 4).

Figure 5:
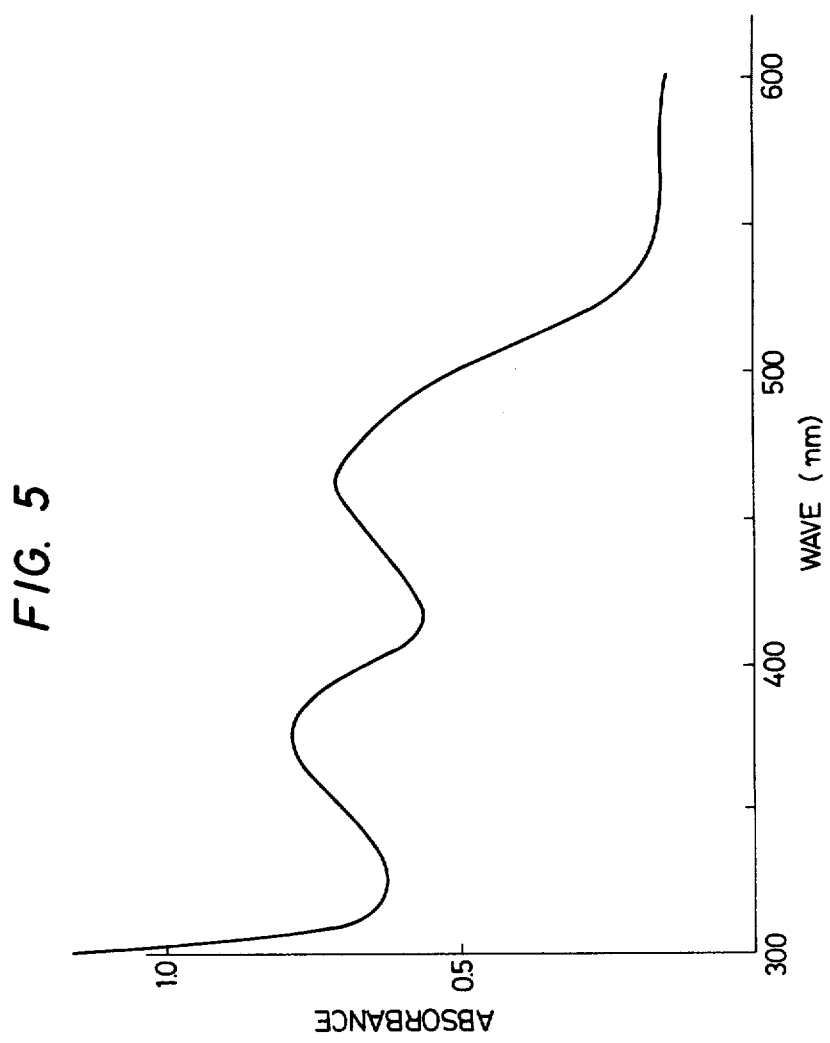
FIG. 5 shows the absorption spectrum in the visible region.

(7) Absorption Spectrum:

From the fact that maximum absorptions are observed at 375 nm and 460 nm in the visible absorption spectrum, it is confirmed that the oxidase is a flavin protein (see FIG. 5).

(8) Influences of Inhibitors and Metal Ions:

(a) Influences of various inhibitors are shown in Table 2.

TABLE 2

| Inhibitor (1.4 mM) | Concentration (10 mM) | Relative Activity (%) |
|---|---|---|
| Hydroxylamine | 1.40 | 100 |
| Hydrazine | 1.40 | 89.7 |
| Phenylhydrazine | 1.40 | 100 |
| Semicarbazide | 1.40 | 85.4 |
| Isoniazid | 1.40 | 94.4 |
| Iproniazid | 1.40 | 72.2 |
| α,α'-Dipyridyl | 1.40 | 97.1 |
| 8-Hydroxyquinoline | 1.40 | 94.0 |
| o-Phenanthroline | 1.40 | 100 |
| Sodium azide | 1.40 | 100 |
| EDTA | 1.40 | 100 |
| PCMB | 8.45 | 81.8 |

TABLE 2-continued

| Inhibitor (1.4 mM) | Concentration (10 mM) | Relative Activity (%) |
|---|---|---|
| Monoiodoacetic acid | 1.40 | 91.2 |

Note
EDTA: ethylenediamine tetraacetate
PCMB: p-chloromercurybenzoate (the unit of the concentration of PCMB is μM)

(b) Influences of metal ions (1.4 mM) are shown in Table 3.

TABLE 3

| Metal Ion | Relative Activity (%) |
|---|---|
| $NH_4^+$ | 80.9 |
| $Ag^+$ | 0.0 |
| $Li^+$ | 84.5 |
| $Ni^{2+}$ | 103.6 |
| $Cu^{2+}$ | 86.4 |
| $Zn^{2+}$ | 69.1 |
| $Mn^{2+}$ | 100 |
| $Mg^{2+}$ | 81.1 |
| $Hg^{2+}$ | 0.0 |
| $Fe^{3+}$ | 81.8 |

(9) Isoelectric Point:

The isoelectric point is 5.0 to 5.25 as measured according to the ampholyte isoelectric point electrophoresis method.

(10) Molecular Weight:

The molecular weight is about 130,000 as determined according to the gel filtration method using Sephadex G-200.

(11) Molecular Weight of Subunit:

The molecular weight of the subunit is about 65,000.

(12) Crystal Form:

The oxidase takes the form of a needle crystal.

Microbial polyamine oxidase AT-1 having the above-mentioned physicochemical properties is a novel polyamine oxidase which is obviously different from polyamine oxidases derived from animals and plants and other polyamine oxidases derived from microorganisms.

In Table 4, properties of this novel polyamine oxidase is compared with properties of polyamine oxidase derived from various origins.

Beef plasma amine oxidase is one disclosed by H. Yamada et al. in The Journal of Biological Chemistry, 237, pages 1511 to 1516 (1962), and rat liver polyamine oxidase is one disclosed by E. Hölltäin Biochemistry, 16, pages 91 to 100 (1977). Pea polyamine oxidase is one disclosed by P. J. G. Mann in Biochemical Journal, 79, pages 623 to 631 (1961) and Method in Enzymology, 17B, pages 730 to 735, and wheat polyamine oxidase is one disclosed by P. A. Smith in Phytochemistry, 13, pages 2437 to 2443 (1974) and ibid, 11, pages 899 to 910 (1972). Serratia marcescens spermidine dehydrogenase is one disclosed by C. W. Tabor et al. in The Journal of Biological Chemistry, 245, pages 5424 to 5433 (1970) and Pseudomonas aeruginosa polyamine oxidase is one disclosed by S. Razin et al. in Biochemical Journal, 71, pages 551 to 558 (1959).

TABLE 4

| | Polyamine oxidase AT-1 of Present Invention | Beef plasma amine Oxidase | Rat Liver Polyamine Oxidase | Pea Polyamine Oxidase |
|---|---|---|---|---|
| Substrate Specificity | reacting only with spermidine and spermine | reacting with spermidine, spermine and other monamine | reacting with spermidine and spermine | strongly reacting with cadaverine and putrescine and reacting with spermidine |
| Decomposition Product of $NH_2(CH_2)_3$-$NH(CH_2)_4NH_2$(spermidine) | $NH_2(CH_2)_2CHO$, $NH_2(CH_2)_4NH_2,H_2O_2$ | $OHC(CH_2)_2NH$-$(CH_2)_4NH_2$, $NH_3, H_2O_2$ | $NH_2(CH_2)_2CHO$, $NH_2(CH_2)_4NH_2$, $H_2O_2$ | $NH_2(CH_2)_3NH$-$(CH_2)_3CHO$, $H_2O_2$, $NH_3$ |
| Decomposition Product of $NH_2(CH_2)_3$-$NH(CH_2)_4NH(CH_2)_3NH_2$ (spermine) | $NH_2(CH_2)_2CHO$, $NH_2(CH_2)_4NH_2,H_2O_2$ | $OHC(CH_2)_2NH$-$(CH_2)_4NH(CH_2)_2$-$CHO$, $NH_3, H_2O_2$ | $NH_2(CH_2)_2CHO$, $NH_2(CH_2)_4NH_2$, $H_2O_2$ | |
| Inhibitor | not inhibited by carbonyl reagent, PCMB or $CH_3COOI$ | | inhibited by carbonyl reagent, PCMB and $CH_3COOI$ | inhibited by carbonyl reagent, chelate compound and $Cu^{2+}$ |
| Optimum pH | 6.5 | 7.2 | about 10 | 7.0 (putrescine) |
| Molecular Weight | 130,000 | 240,000 | 55,000–61,000 | 96,000 |
| Isoelectric Point | 5.0–5.25 | | 4.9 | |
| Coenzyme, etc. | FAD | $Cu^{2+}$ | FAD | $Cu^{2+}$ |

| | Barley Polyamine Oxidase | Serratia spermidine dehydrogenase | Pseudomonas Polyamine Oxidase |
|---|---|---|---|
| Substrate Specificity | strongly reacting with spermine and reacting with spermidine | strongly reacting with putrescine and spermidine and reacting with spermine | reacting with spermidine, spermine, cadaverine, putrescine and agmatine |
| Decomposition Product of $NH_2(CH_2)_3$-$NH(CH_2)_4NH_2$(spermidine) | $NH_2(CH_2)_3CHO$, $NH_2(CH_2)_3NH_2$, $H_2O_2$ | $NH_2(CH_2)_3CHO$, $NH_2(CH_2)_3NH_2$ | $NH_2(CH_2)_3NH_2$, $NH_2(CH_2)_3CHO$ |
| Decomposition Product of $NH_2(CH_2)_3$-$NH(CH_2)_4NH(CH_2)_3NH_2$ (spermine) | $NH_2(CH_2)_3NH(CH_2)_3$-$CHO$, $NH_2(CH_2)_3NH_2$, $H_2O_2$ | $NH_2(CH_2)_3NH$-$(CH_2)_3CHO$, $NH_2(CH_2)_3NH_2$ | $NH_2(CH_2)_3NH(CH_2)_4NH_2$, $NH_2(CH_2)_2CHO$ |

TABLE 4-continued

| Inhibitor | | | |
|---|---|---|---|
| Optimum pH | 6.5 (spermidine), 4.5 (spermine) | 6.5 | 7.0–7.2 |
| Molecular Weight | | 76,000 | |
| Isoelectric Point | | | |
| Coenzyme, etc. | FAD | FAD | |

As will be apparent from Table 4, none of polyamine oxidases derived from animals, plants and microorganisms are in agreement with polyamine oxidase AT-1 of the present invention in all of the substrate specificity, the mode of decomposition of spermidine and spermine, the behavior to inhibitors, the optimum pH values, the molecular weight and the isoelectric point.

Novel polyamine oxidase AT-1 is obtained by culturing *Aspergillus terreus* IFO 6346. Any of synthetic and natural culture media containing appropriate amounts of carbon sources, nitrogen sources, inorganic substances and other nutrients may be used. Either liquid media or solid media may be used, but a liquid medium is ordinarily used. At least one polyamine oxidase AT-1 inducer such as spermidine or spermine is appropriately incorporated in such culture medium.

The cultivation conditions will now be described. The pH value at the start of culturing is ordinarily 4.0 to 7.0 and preferably about 5.0 to about 6.0. The culturing temperature is ordinarily 20° to 40° C. and preferably 25° to 35° C. If cultivation is conducted under these conditions for 12 to 120 hours, polyamine oxidase AT-1 is formed and accumulated in a large amount in the culture product.

Polyamine oxidase AT-1 thus formed and accumulated in the culture product is collected according to the following procedures. Since polyamine oxidase AT-1 present mainly in cells, after completion of cultivation, the cells are collected by filtration or the like, washed with water or a buffer solution and suspended in an appropriate amount of a buffer solution to extract polyamine oxidase AT-1 contained in the cells.

Furthermore, polyamine oxidase AT-1 released from the cells into the culture liquid can be recovered from the filtrate according to customary procedures.

Crude polyamine oxidase AT-1 obtained from the cell extract or culture broth may be purified by isoelectric point precipitation, ion exchange chromatography, fractionating precipitation with ammonium sulfate, column chromatography using hydroxyapatite and gel filtration using Sephadex, while combining these purifying means appropriately or repeating these treatments. Other customary purifying methods may also be adopted according to need.

Polyamine oxidase AT-1 liquid of a high purity which has been thus purified shows a single spot at the disc electrophoresis, and a needle crystal is obtained by concentration and crystallization with ammonium sulfate.

The method used in the present invention for determining the activity of polyamine oxidase AT-1 will now be described.

In 100 ml of a 0.1 M potassium phosphate buffer solution (having a pH value of 6.5) are dissolved 10 mg of 4-aminoantipyrine, 0.2 ml of phenol and 10 mg of peroxidase, and 0.5 ml of spermine (10 mM) or spermidine (10 mM) and 0.5 ml of the enzyme solution are added to 15 ml of the so formed coloring reagent and reaction is carried out at 35° C. The quantity of the change of the absorbance at 505 nm per minute is measured. The polyamine oxidase activity units of the enzyme solution are calculated in the following manner. The amount of the polyamine oxidase forming 1.0 $\mu$M of hydrogen peroxide per minute is defined as 1 unit. This one unit of the polyamine oxidase corresponds to increase of 0.008 of the absorbance at 505 nm per minute.

The new procedures to determine putrescine, spermidine and spermine are firstly established by the end point assay method using polyamine oxidase AT-1 and putrescine oxidase.

Method 1: Spermidine and spermine were first oxidized with polyamine oxidase (step A). To the reaction mixture, putrescine oxidase was added to oxidize putrescine (step B). Putrescine and spermidine in another reaction mixture were oxidized with putrescine oxidase (step C).

Method 2: Putrescine and spermidine were first oxidized with putrescine oxidase (step A). To the reaction mixture, polyamine oxidase was added to oxidize spermine (step B). Spermidine and spermine in another reaction mixture were oxidized with polyamine oxidase (step C). The amounts of putrescine, spermidine and spermine were determined from the absorbance values at each step A, B and C.

The present invention will now be described with reference to the following Example.

EXAMPLE 1

*Aspergillus terreus* IFO 6346 was inoculated on 8 l of a culture medium comprising 0.1% of $NaNO_3$, 0.1% of $KH_2PO_4$, 0.05% of $MgSO_4.7H_2O$, 0.05% of KCl and 3.0% of glucose and cultivation was conducted at 28° C. for 48 hours. The so obtained seed culture liquid was added to 80 l of a culture medium comprising 0.1% of glucose, 0.1% of $KH_2PO_4$, 0.15% of $KH_2PO_4$, 0.02% of $MgSO_4.7H_2O$ and 0.025% of spermidine (the pH value before sterilization was 5.5), and culturing was conducted for 72 hours while adding 0.025% of spermidine at the points of 12, 24 and 36 hours from the start of culturing, respectively. Cells (3.5 Kg) were collected by filtration after culturing, washed with a 0.01 M potassium phosphate buffer solution (the pH value was 6.8), suspended in the same buffer solution and disrupted by a Dino mill. The supernatant (7780 ml) (the extract containing 58.8 U/ml) was obtained by centrifugal separation (7000 rpm and 20 minutes) of the disrupted cell liquid. The extract was immediately passed through a column packed with 1.8 l of DEAE-cellulose equilibrated by a 0.01 M potassium phosphate buffer solution (the pH value was 6.8) to make polyamine oxidase AT-1 adsorbed on the cellulose. Then, the column was washed with a 0.1 M potassium phosphate buffer solution (the pH value was 6.8) and eluted by the linear concentration gradient method. The eluted active fraction was subjected to ammonium sulfate fractionation at a concentration corresponding to 50 to 90% of the saturation concentration of ammonium sulfate, followed by dialysis with a 0.01 M potassium phosphate buffer solution (the pH value was 6.0). The dialyzed enzyme solution was passed through a column packed with hydroxyapatite equilibrated with the same buffer solution as described above to make the active fraction adsorbed on hydroxyapatite, and the column was washed with a 0.01 M potassium phosphate buffer solution (the pH value was 6.0) and the active fraction was eluted by the linear concentration gradient method, and the eluate was concentrated with an ammonium sulfate solution having a concentration corresponding to 90% of the saturation concentration and passed through a molecular sieve of Sephade G-200. The active fraction of polyamine oxidase AT-1 contained in the solution which had been passed through the molecular sieve was concentrated and crystallization was effected by addition of ammonium sulfate. A needle crystal was obtained. The activity recovery ratio throughout all the steps for recovery of such crystal was about 15.0%.

Differential determination of putrescine, spermidine and spermine by using polyamine oxidase AT-1 will be shown.

Method 1: In the presence of putrescine, spermidine and spermine, spermidine and spermine are first oxidized with polyamine oxidase AT-1 at pH 6.5. After completion of the reaction, its pH was adjusted to around 8.5 and the absorbance value (by 505 nm) is measured (step A). At step A, putrescine is not oxidized. Spermidine and spermine are completely oxidized to putrescine.

The absorbance change at step A shows the molar concentrations of spermidine plus twice of spermine. Putrescine oxidase is then added to the reaction mixture at step A, and the reaction is continued until putrescine is completely oxidized (step B). At step B, total putrescine, which consisted of firstly presented one and that produced by polyamine oxidations at step A, are oxidized. Therefore, the absorbance change at step B shows the total concentrations of putrescine plus spermidine plus spermine. Where as the absorbance value, which is measured at the end of step B, shows the absorbance change at step A plus that at step B, the absorbance change at step B is obtained by subtracting the absorbance value at step A from that at step B. When another reaction mixture containing putrescine, spermidine and spermine is also oxidized with putrescine oxidase at pH 8.5, putrescine and spermidine are completely oxidized (step C). The absorbance change at step C shows the concentrations of putrescine plus spermidine. From these results, the absorbance changes at steps A, B and C ($Y_a$, $Y_b$, $Y_c$) were defined by eqs. 1, 2 and 3, respectively.

$$Y_a = [SPD] + 2[SPM] \tag{1}$$

$$Y_b = [PUT] + [SPD] + [SPM] \tag{2}$$

$$Y_c = [PUT] + [SPD] \tag{3}$$

Where, [PUT], [SPD] and [SPM] represent the concentrations of putrescine, spermidine and spermine, respectively. Therefore, the concentrations or the amounts of putrescine, spermidine and spermine could be calculated as follows.

$$[PUT] = 2Y_b - Y_a - Y_c \tag{4}$$

$$[SPD] = Y_a + 2Y_c - 2Y_b \tag{5}$$

$$[SPM] = Y_b - Y_c \tag{6}$$

Method 2: In the presence of putrescine, spermidine and spermine, putrescine and spermidine are first oxidized with putrescine oxidase at pH 8.5. After completion of the reaction, its pH was adjusted to around 6.5 and the absorbance value (by 505 nm) is measured (step A). Step A is identical to step C of Method 1, in which the absorbance change shows the concentrations of putrescine plus spermidine. Polyamine oxidase AT-1 is then added to the reaction mixture at step A, and the reaction is continued until spermine is completely oxidized (step B). The absorbance change at step B shows twice of molar concentration of spermine. Where as the absorbance value, which was measured at the end of step B, shows the absorbance change at step A plus that at step B, the absorbance change at step B was obtained by subtracting the absorbance value at step A from that at step B. When another reaction mixture containing putrescine, spermidine and spermine is oxidized with polyamine oxidase AT-1 at pH 6.5, spermidine and spermine are completely oxidized without oxidation of putrescine just as step A of Method 1. The absorbance change at step C shows the molar concentrations of spermidine plus twice of spermine. From these results, the absorbance changes at steps A, B and C ($Y_a$, $Y_b$, $Y_c$) are defined by eqs. 7, 8 and 9, respectively.

$$Y_a = [PUT] + [SPD] \tag{7}$$

$$Y_b = 2[SPM] \tag{8}$$

$$Y_c = [SPD] + 2[SPM] \tag{9}$$

Therefore, the concentrations or the amounts of putrescine, spermidine and spermine could be calculated by eqs. 10, 11 and 12.

$$[PUT] = Y_a + Y_b - Y_c \tag{10}$$

$$[SPD] = Y_c - Y_b \tag{11}$$

$$[SPM] = \tfrac{1}{2} Y_b \tag{12}$$

What is claimed is:

1. Microbial polyamine oxidase AT-1 having the following physicochemical properties:

(1) Reactivity:
   it reacts with spermidine to form 1 mol of putrescine, 1 mol of 3-aminopropionaldehyde and 1 mol of hydrogen peroxide from 1 mol of spermidine and it reacts with spermine to form 1 mol of putrescine, 2 mol of 3-aminopropionaldehyde and 2 mol of hydrogen peroxide from 1 mol of spermine;

(2) Substrate specificity:
   it oxidizes spermidine and spermine at a rate of 2:1, but it does not substantially react with other amines;

(3) Optimum pH value:
   the optimum pH value is about 6.5;

(4) pH Stability:
   when it is treated at 30° C. for 30 minutes, the residual ratio of the activity at a pH value from 5.2 to 6.5 is higher than 90%;

(5) Optimum temperature:
   the optimum temperature is about 50° C. at a pH value of 6.5 and the optimum temperature is about 45° C. at a pH value of 7.0;

(6) Temperature stability:

when it is treated at 30° C. for 10 minutes at a pH value of 6.5, the residual ratio of the activity is higher than 90%;

(7) Absorption spectrum:
from the fact that maximum absorptions are observed at 375 nm and 460 nm in the absorption spectrum, it is confirmed that the oxidase is a flavin protein;

(8) Influences of inhibitors and metal ions:
the activity is strongly inhibited by metal ions such as a silver ion and a mercury ion;

(9) Isoelectric point:
the isoelectric point is 5.0 to 5.25;

(10) Molecular weight:
the molecular weight is 130,000 as determined according to the gel filtration method using Sephadex G-200;

(11) Molecular weight of subunit:
the molecular weight of the subunit is 65,000 as determined according to the SDS disc electrophoresis method;

(12) Crystal form:
it takes the form of a needle crystal.

* * * * *